US008874623B2

(12) United States Patent
Sanchez Loureda et al.

(10) Patent No.: US 8,874,623 B2
(45) Date of Patent: Oct. 28, 2014

(54) DATA STORAGE AND TRANSFER

(75) Inventors: Jose Manuel Sanchez Loureda, London (GB); Adam Richard Westbrooke, Kent (GB); Edward Horsford, London (GB); Brian McGuigan, London (GB)

(73) Assignee: Onzo Limited, London (GB)

( * ) Notice: Subject to any disclaimer, the term of this patent is extended or adjusted under 35 U.S.C. 154(b) by 0 days.

(21) Appl. No.: 13/061,101

(22) PCT Filed: Nov. 12, 2010

(86) PCT No.: PCT/GB2010/002091
§ 371 (c)(1),
(2), (4) Date: Aug. 17, 2011

(87) PCT Pub. No.: WO2011/058326
PCT Pub. Date: May 19, 2011

(65) Prior Publication Data
US 2011/0295912 A1 Dec. 1, 2011

(30) Foreign Application Priority Data

Dec. 11, 2009 (GB) .................................. 0919785.6
Dec. 18, 2009 (GB) .................................. 0922164.9

(51) Int. Cl.
| | | |
|---|---|---|
| G06F 17/30 | (2006.01) | |
| G01D 4/00 | (2006.01) | |
| G01D 3/032 | (2006.01) | |
| G01N 29/44 | (2006.01) | |

(52) U.S. Cl.
CPC ................ *G01D 3/032* (2013.01); *G01D 4/004* (2013.01); *Y04S 20/38* (2013.01); *Y02B 90/242* (2013.01); *Y04S 20/322* (2013.01); *Y04S 20/242* (2013.01); *G01N 29/4463* (2013.01); *Y02B 70/3266* (2013.01)

USPC ................. 707/812; 702/57; 702/60; 702/61; 702/127; 324/160; 324/207.23

(58) Field of Classification Search
USPC ......... 707/812; 702/57, 127, 60–61; 324/160, 324/207.23
See application file for complete search history.

(56) References Cited

U.S. PATENT DOCUMENTS

| | | |
|---|---|---|
| 4,335,447 A | 6/1982 | Jerrim et al. |
| 4,858,141 A | 8/1989 | Hart et al. |

(Continued)

FOREIGN PATENT DOCUMENTS

| | | |
|---|---|---|
| CN | 201210176 | 3/2009 |
| DE | 19535719 | 3/1997 |

(Continued)

OTHER PUBLICATIONS

Intellectual Property Office, Search Report under Section 17 for GB0922164.9, dated Apr. 21, 2011.

(Continued)

*Primary Examiner* — Hanh Thai
(74) *Attorney, Agent, or Firm* — Arent Fox LLP (57) ABSTRACT

A method and apparatus for storing data regarding parameter values by making a series of measurements of parameter values at times separated by predetermined time intervals, processing the series of measurements of parameter values made at predetermined time intervals to identify events at different times, generating a further series of measurements of parameter values at each of said different times, and storing each of said further series of measurements of parameter values in association with said respective different time.

18 Claims, 3 Drawing Sheets

(56) References Cited

U.S. PATENT DOCUMENTS

| | | | |
|---|---|---|---|
| 5,483,153 A | 1/1996 | Leeb et al. | |
| 5,600,576 A | 2/1997 | Broadwater et al. | |
| 6,195,018 B1* | 2/2001 | Ragle et al. | 340/870.01 |
| 6,470,283 B1 | 10/2002 | Edel | |
| 6,507,794 B1 | 1/2003 | Hubbard et al. | |
| 6,826,513 B1 | 11/2004 | Kumar et al. | |
| 6,885,309 B1* | 4/2005 | Van Heteren | 340/870.11 |
| 7,146,288 B1 | 5/2006 | Welch et al. | |
| 7,260,272 B2 | 8/2007 | Lin et al. | |
| 7,353,245 B2 | 4/2008 | Healey et al. | |
| 7,379,791 B2 | 5/2008 | Tamarkin | |
| 7,467,170 B1 | 12/2008 | Chen | |
| 7,502,698 B2 | 3/2009 | Uenou | |
| 7,511,609 B2 | 3/2009 | Hammerschmidt | |
| 7,639,129 B2 | 12/2009 | Bickel | |
| 7,693,670 B2 | 4/2010 | Durling et al. | |
| 7,765,034 B2* | 7/2010 | Gardner et al. | 700/286 |
| 8,103,465 B2 | 1/2012 | Brzezowski | |
| 8,150,950 B2 | 4/2012 | McQuillan | |
| 8,156,055 B2* | 4/2012 | Shimada et al. | 706/12 |
| 8,201,105 B2 | 6/2012 | Tabe | |
| 8,214,270 B2 | 7/2012 | Schaefer | |
| 8,271,147 B2 | 9/2012 | Beal | |
| 2001/0011278 A1 | 8/2001 | Shimokawa | |
| 2003/0158826 A1 | 8/2003 | Burke | |
| 2004/0008904 A1 | 1/2004 | Lin | |
| 2004/0044713 A1* | 3/2004 | Healey et al. | 708/322 |
| 2004/0153170 A1* | 8/2004 | Santacatterina et al. | 700/1 |
| 2005/0057348 A1* | 3/2005 | Hammerschmidt | 340/445 |
| 2005/0190074 A1 | 9/2005 | Cumeralto | |
| 2006/0031180 A1 | 2/2006 | Tamarkin | |
| 2007/0013499 A1* | 1/2007 | Hammerschmidt | 340/442 |
| 2007/0241739 A1* | 10/2007 | Uenou et al. | 324/76.17 |
| 2007/0279494 A1* | 12/2007 | Aman et al. | 348/169 |
| 2008/0001600 A1* | 1/2008 | deCharms | 324/309 |
| 2008/0079741 A1 | 4/2008 | Martin | |
| 2008/0136409 A1* | 6/2008 | Sen et al. | 324/303 |
| 2009/0045804 A1* | 2/2009 | Durling et al. | 324/140 R |
| 2009/0066528 A1* | 3/2009 | Bickel et al. | 340/657 |
| 2009/0088991 A1* | 4/2009 | Brzezowski et al. | 702/62 |
| 2009/0179642 A1* | 7/2009 | deCharms | 324/309 |
| 2009/0282275 A1* | 11/2009 | Yermalayeu et al. | 713/320 |
| 2009/0287803 A1 | 11/2009 | McQuillan et al. | |
| 2009/0307178 A1 | 12/2009 | Kuhns | |
| 2010/0152600 A1* | 6/2010 | Droitcour et al. | 600/534 |
| 2010/0174643 A1 | 7/2010 | Schaefer | |
| 2010/0217450 A1 | 8/2010 | Beal | |
| 2010/0217452 A1 | 8/2010 | McCord | |
| 2011/0004421 A1 | 1/2011 | Rosewell | |
| 2011/0213556 A1 | 9/2011 | Yu et al. | |
| 2012/0197594 A1 | 8/2012 | Orth | |

FOREIGN PATENT DOCUMENTS

| | | |
|---|---|---|
| EP | 295864 | 9/1990 |
| EP | 1309062 | 3/2004 |
| EP | 0863596 | 3/2008 |
| EP | 2026299 | 2/2009 |
| EP | 2237212 | 10/2010 |
| EP | 2141464 | 9/2011 |
| GB | 1012499 | 12/1965 |
| GB | 2420863 | 6/2006 |
| GB | 2409048 | 7/2007 |
| GB | 2461915 | 12/2010 |
| GB | 2472251 | 2/2011 |
| GB | 2471536 | 6/2011 |
| GB | 1108357.3 | 9/2013 |
| JP | 4976158 | 7/2012 |
| WO | WO 03026346 | 3/2004 |
| WO | WO 2008142431 | 11/2008 |
| WO | WO 2008142431 | 1/2009 |
| WO | WO 2009081407 | 7/2009 |
| WO | WO 2009014995 | 8/2009 |
| WO | WO 2009103998 | 8/2009 |
| WO | WO 2010007369 | 3/2010 |
| WO | WO 2010129414 | 11/2010 |
| WO | WO 2010106253 | 12/2010 |
| WO | WO 2011058328 | 9/2011 |
| WO | WO 2011000356 | 1/2012 |
| WO | WO 2012156758 | 11/2012 |

OTHER PUBLICATIONS

GB Further Search dated Aug. 5, 2011 regarding Application No. GB0922164.9.
GB Examination Report dated Aug. 22, 2012 regarding Application No. GB0922164.9.
GB Examination Report dated Jan. 8, 2013 regarding Application No. GB0922164.9.
GB Search Report dated Nov. 19, 2010 regarding Application No. GB1012499.8.
GB Examination Report dated Aug. 21, 2012 regarding Application No. G81012499.8.
GB Search Report dated May 10, 2011 regarding Application No. GB0919785.6.
GB Combined Search and Examination Report dated May 11, 2011 regarding Application No. 080919785.6.
GB Further Search Report dated Jun. 15, 2011 regarding Application No. 080919785.6.
GB Search Report dated Mar. 18, 2011 regarding Application No. GB1011192.0.
GB Further Search Report dated Jun. 9, 2011 regarding Application No. GB1011192.0.
GB Search Report dated Aug. 22, 2012 regarding Application No. GB1011192.0.
GB Examination Report dated Dec. 24, 2012 regarding Application No. GB1011192.0.
Later Publication dated May 19, 2011 and International Search Report regarding Application No. PCT/GB2010/002091.
International Search Report dated Aug. 31, 2011 regarding Application No. PCT/GB2010/002091.
IPRP dated May 15, 2012 and Written Opinion regarding Application No. PCT/GB2010/002091.
Publication dated May 19, 2011 and International Search Report regarding Application No. PCT/GB2010/002092.
International Search Report dated Jul. 14, 2011 regarding Application No. PCT/GB2010/002092.
IPRP dated May 15, 2012 and Written Opinion regarding Application No. PCT/GB2010/002092.
XP031881193—Extensible Biosignal Metadata a Model for Physiological Timeseries Data—Brooks D., Sep. 2-6, 2009.
XP000336363—Nonintrusive Appliance Load Monitoring—Hart G W
ViridiScope: Design and Implementation of a Fine Grained Power Monitoring System for Homes—Kim et al.
Ian Kaplan, Applying the Haar Wavelet Transform to Time Series information, Feb. 2004, retrieved from http://www.bearcave.com/misl/misl_tech/wavelets/haar.html#HaarWavelets. See subpage Wavelet Noise Thresholding, Aug. 2001, retrieved from http://www.hearcave.com/misl/misl_tech/wavelets/noise.html.
Residential Baseload Energy Use: Concept and Potential for AMI Customers—Nelson et al., Year 2008.
David L. Donoho and Ian M. Johnstone, Ideal spatial adaptation by wavelet shrinkage, Biometrika (1994), 81, 3, pp. 425-455. Retrieved from http://www.stanford.edu/~slansel/tutorial/Papers/Donoho/Ideal%20Spatial%20Adaptation%20by%2OWavelet%20Shrinkage.pdf—See pp. 429-445.
European Search Report & Search Opinion for EP12183390.9, mailed Jan. 25, 2013.

* cited by examiner

DATA STORAGE AND TRANSFER

FIELD OF THE INVENTION

This invention relates to methods, systems, devices and computer code for storage and transfer of data, particularly data associated with consumption of utilities such as gas, water and electricity, and to transfer the stored utility consumption data for applications such as analysis of household power consumption by an end-user or by a utility supplier, or monitoring occupancy and activity within a household.

BACKGROUND

There is an ongoing and urgent need to reduce consumption of energy and water both for environmental and cost reasons.

A large proportion of the energy and water supplied by utilities suppliers is wasted as a result of inefficiencies such as use of electrical appliances that have poor efficiency or for behavioural reasons such as appliances that are left switched on and so consume electricity even when not in use, or excessive consumption of water. This leads to wastage and increased utilities costs. Moreover, with respect to electricity, electrical energy use in buildings accounts for a very large proportion of all carbon emissions. Demand for utilities can vary dramatically between identical buildings with the same number of occupants, and this suggests that reducing waste through behavioural efficiency is essential. Therefore, efforts are required to change the patterns of utilities use by consumers.

The utilities suppliers recognise three major obstacles to progress in this objective: a shortage of sources of competitive advantage, a lack of detailed understanding of their customers, and a lack of "touch points", i.e. ways of interacting with the customers. Opportunities for differentiation revolve mainly around price and "green" issues, i.e. reduction of environmental impact. The utilities suppliers have very little information about their customers' behaviour since electricity, gas and water meters collect whole house data continuously and are read infrequently.

Meters to measure total consumption of utilities of a household are commonplace for each of gas, electricity and water, however this total is not useful in identifying areas in which efficiencies may be possible (for brevity, we refer herein to a "household", however it will be appreciated that the present invention is not limited to a domestic house but may be applied to any domestic, workplace or other setting that receives its own discrete utilities supplies, in particular mains electricity supply from an electricity grid; water supply; and/or gas supply.).

Apparatus for monitoring consumption of a resource such as electricity supplied on a cable is disclosed in WO 2008/142425. While a meter of this type is beneficial in assisting a user to review energy consumption patterns, when the meter is operated in a high resolution mode, for example measuring power consumption at one second intervals, there is a problem in storing the relatively large amount of power consumption data produced by the meter. Further, when the power consumption data is stored by the meter and subsequently sent to a remote device for display or analysis of resource consumption there is a problem in selecting and transferring the relatively large amount of power consumption data stored by the meter. Further, when the power consumption data is stored by the meter and subsequently sent to a remote device for display or analysis of resource consumption, if communication between meter and the remote device is interrupted there can be problems in selecting and transferring stored power consumption data to the remote device.

It is therefore an object of the invention to provide technical means for storage, recovery and transmission of utilities consumption data in a household.

SUMMARY OF THE INVENTION

According to a first aspect the invention provides a method of storing data regarding parameter values comprising the steps of:
  making a series of measurements of parameter values at times separated by predetermined time intervals;
  processing the series of measurements of parameter values made at predetermined time intervals to identify events at different times;
  generating a further series of measurements of parameter values at each of said different times; and
  storing each of said further series of measurements of parameter values in association with said respective different time.

In a second aspect, the invention provides a data processing apparatus adapted to carry out the method of the first aspect.

In a third aspect, the invention provides a data processing apparatus adapted to store data regarding utilities consumption comprising:
  sensor means adapted to make a series of measurements of utilities consumption values at times separated by predetermined time intervals;
  data processor means adapted to process the series of measurements of utilities consumption values made at predetermined time intervals to identify events at different times;
  data processor means adapted to generate a further series of measurements of utilities consumption values at each of said different times;
  storage means adapted to store each of said further series of measurements of utilities consumption values in association with said respective different time; and
  transmitter means adapted to transmit the stored measurements of parameter values and associated times to a data processor.

In a fourth aspect, the invention provides a data processing apparatus adapted to store data regarding electricity consumption comprising:
  sensor means adapted to make a series of measurements of electricity consumption values at times separated by predetermined time intervals;
  data processor means adapted to process the series of measurements of electricity consumption values made at predetermined time intervals to identify events at different times;
  data processor means adapted to generate a further series of measurements of electricity consumption values at each of said different times;
  storage means adapted to store each of said further series of measurements of electricity consumption values in association with said respective different time; and
  transmitter means adapted to transmit the stored measurements of parameter values and associated times to a data processor.

In a fifth aspect, the invention provides a system comprising apparatus according to the second aspect or the third aspect, and further comprising a data processor adapted to receive the transmitted stored measurements of parameter values and associated times.

In a sixth aspect, the invention provides a computer program product adapted to perform the method of the first aspect.

In a seventh aspect, the invention provides a computer program comprising software code adapted to perform the method of the first aspect.

In an eighth aspect, the invention provides a computer program comprising software code adapted to perform steps of:

making a series of measurements of electricity consumption values at times separated by predetermined time intervals;
  processing the series of measurements of electricity consumption values made at predetermined time intervals to identify events at different times;
  generating a further series of measurements of electricity consumption values at each of said different times; and
  storing each of said further series of measurements of electricity consumption values in association with said respective different time; and
  transmitting the stored measurements of parameter values and associated times to a data processor.

In a ninth aspect, the invention provides a computer readable storage medium comprising the program of any one of the sixth to eighth aspects.

In a tenth aspect, the invention provides a computer program product comprising computer readable code according to the ninth aspect.

In an eleventh aspect, the invention provides an integrated circuit configured to perform the steps according to the first aspect of the invention.

In a twelfth aspect, the invention provides an article of manufacture comprising: a machine-readable storage medium; and executable program instructions embodied in the machine readable storage medium that when executed by a programmable system causes the system to perform the function of storing data regarding utilities consumption comprising the steps of:
  making a series of measurements of parameter values at times separated by predetermined time intervals;
  processing the series of measurements of parameter values made at predetermined time intervals to identify events at different times;
  generating a further series of measurements of parameter values at each of said different times; and
  storing each of said further series of measurements of parameter values in association with said respective different time.

In a thirteenth aspect, the invention provides a data structure storing electrical utility supply data, the data structure comprising a series of stored data clusters, wherein each stored data cluster comprises in association:

a real power value of an electricity supply at a specific time;
  a reactive power value of an electricity supply at said time; and said time;
  wherein the specific times of successive data clusters in the series are separated by a variable time interval.

In a forteenth aspect, the invention provides a signal comprising electrical utility supply data, the signal comprising a series of data clusters, wherein each data cluster comprises in association:

a real power value of an electricity supply at a specific time;
  a reactive power value of an electricity supply at said time; and said time;
  wherein the specific times of successive data clusters in the series are separated by a variable time interval.

The invention further provides systems, devices, computer-implemented apparatus and articles of manufacture for implementing any of the aforementioned aspects of the invention; computer program code configured to perform the steps according to any one of the aforementioned methods; a computer program product carrying program code configured to perform the steps according to any one of the aforementioned methods; and a computer readable medium carrying the computer program.

DESCRIPTION OF FIGURES

The invention will now be described in detail with reference to the following figures in which.

DETAILED DESCRIPTION OF THE INVENTION

Figure 1:
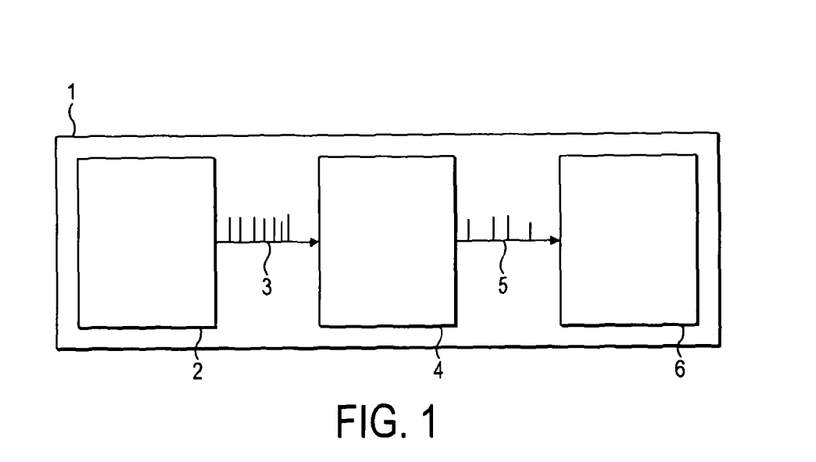
FIG. 1 is a diagram of a smart meter according to the invention.

An example of apparatus for carrying out the method according to the present invention is illustrated in FIG. 1 with respect to electricity consumption. The method may be divided into three broad steps:

(1) Measurement of electrical consumption data at regularly spaced time measurement points;

(2) Identification of events based in particular on changes in electricity demand, in particular power, between measurement points; and (3) Storing identified events together with a timestamp.

Each of these steps is described in more detail below. While the invention is described hereinafter primarily with respect to measurement, analysis and storage of electricity consumption data, it will be appreciated that the same steps may equally be taken using data relating to consumption of gas or water, or other utilities. Further, although the invention is described herein primarily with respect to electrical power measurement, it will be appreciated that other electrical parameters could be measured, for example admittance, frequency, harmonic distortion, voltage, etc.

Measurement

A smart meter 1 comprises a sensing device 2 which measures consumed electrical power for a household, or other setting that receives its own discrete utilities, at fixed interval time points, generating a series of measurements 3 at fixed intervals. A higher frequency of measurement will obviously yield more electricity consumption data, which in turn will generally increase the usefulness and value of the measured data. Typically, electricity consumption is measured at least once every second.

The sensing device 2 measures consumed electrical power by measuring both real power and reactive power. This is captured as two separate streams of data, one stream comprising measurements of real power, and the other stream comprising measurements of reactive power ("real power" and "reactive power" as used herein have the meanings as understood by a skilled person in the art in relation to power supplied to a load from an alternating current source). For simplicity, only a single stream of measurements 3 is shown in FIG. 1, where the measurements 3 are two dimensional measurements, where each measurement 3 comprises both a real power measurement and a reactive power measurement made at the same time. It would of course be possible for the real power and reactive power values to be treated or shown as separate streams of measurement.

One advantage of measuring both real and reactive power is that, between them, it is possible to measure power demand of most or all appliances. For instance, it may be difficult or impossible to obtain a meaningful measurement of real power for certain appliances such as set-top boxes, however reactive power for these devices can be measured.

The sensing device 2 could be a clamp on energy meter as disclosed in WO 2008/142431.

Although the series of measurements 3 are described as being at fixed intervals this is intended only to indicate that they are at fixed intervals during operation. The sensing device 2 may be able to carry out measurements at a range of different time intervals so that the actual time interval used in a specific application can be set to a suitable value.

Event Identification

As shown in FIG. 1, the series of fixed interval power measurements 3, comprising consumption data readings relating to real and reactive power made at fixed intervals in the measurement step by the sensing device 2, is fed into an event identifying device 4. The event identifying device 4 processes the received series of fixed interval power measurements 3 in order to identify significant changes in the value of the measured power which correspond to events of interest.

The event identifying device 4 carries out this identifying by using an event identifying algorithm, which processes the fixed interval power measurements 3 and compares changes in values of parameters of the fixed interval power measurements 3 to selected criteria and thresholds in order to identify changes in the values which correspond to events of interest. It will be understood that there are many ways of carrying out such identification, and in any specific application of the invention it will be necessary to select a suitable event identifying algorithm which is appropriate to the fixed interval measurements being made and the events which it is desired to identify. One example of an event identifying algorithm which is suitable for processing fixed interval power measurements to identify events is discussed in detail below.

When the event identifying device 4 identifies an event it generates a respective event measurement 5 corresponding to the event and comprising the relevant measured event parameter values together with a timestamp which indicates the time at which the event took place. Accordingly, the event identifying device 4 generates as an output a series of event measurements 5 at variable intervals. It will be understood that the intervals between the event measurements 5 in the series of event measurements are variable because the timing of the event measurements 5 depends on the timing of the identified events. Since the identified events are "real world" events their timing is inherently variable.

In the described embodiment each variable interval event measurement 5 comprises the real and reactive power consumption value measurements at the time of the identified event together with the corresponding timestamp. Thus, the event parameter values of the event measurements 5 are derived from the fixed interval measurements, in this embodiment the fixed interval power measurements, by selection. It will be understood that other forms of derivation are possible. The form of derivation used may be selected based upon the details of the event identifying algorithm.

Optionally, each variable interval event measurement 5 can also comprise further parameter values relating to the event and produced during the processing. For example, the further parameter values could be value measurements of admittance, frequency, harmonic distortion, or voltage. In practice, whether such further parameter values are desired, and if so, what the further parameters are, will depend upon what processing is applied and the intended use of the variable interval event measurement 5 in each case.

As stated above, each event measurement 5 corresponds to a respective event. It will be understood that the generation of each event measurement 5 implicitly identifies that some event has taken place. However, it is not required that the type of the event is identified by the event measurement 5, although this could optionally be done.

The event identifying device may be provided by software running on a processor of the smart meter. Alternatively, the event identifying device may be provided by hardware in the form of an application specific integrated circuit (ASIC) in the smart meter.

Event Storage

The series of event measurements 5 at variable intervals from the event identifying device 4 is fed to a memory device 6 where the event measurements 5, including their respective timestamps, are stored.

In practice, it has been found that most of the measurements 3 at fixed intervals are not associated with events of interest. As a result, use of the present invention reduces the amount of data which must be stored in order to allow power consumption to be tracked over time, and in order to allow the power consumption history to be reproduced from the stored data. It is possible that over some short periods when there are an unusually large number of events there may be no reduction in the amount of data which must be stored. However, even in these cases, there will still be an overall reduction over longer periods.

Thus, the amount of data recording the power consumption can be compressed. This data compression is a lossy compression because the data regarding fixed interval measurements which are not associated with an event of interest is not recorded.

The degree of compression will depend, among other things, on the number, or frequency, of events relative to the number, or frequency, of fixed interval measurements. Thus, for any specific number of events, the degree of compression will increase as the time interval between the fixed interval measurements decreases, that is, as their frequency increases.

The depiction of different functional parts of the smart meter as different elements in the figures does not indicate that the functions must be necessarily provided by separate physical components.

Corner Detection

A specific example of an event detection algorithm, referred to hereinafter as a "corner detection algorithm", which can be used in the present invention will now be described in detail.

Figure 3:
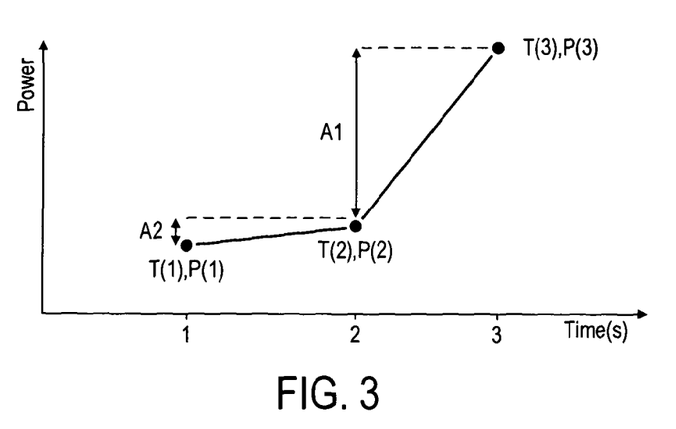
FIG. 3 illustrates the identification of "corners" in electricity consumption data.

The operation of the corner detection algorithm is illustrated schematically in FIG. 3. The compression algorithm identifies "corners" in power demand by identifying differences in the gradient representing rate of change in power from one fixed interval time point to the next. These corners in power demand are regarded as events of interest in the present invention.

A point at which there is change in gradient between two successive time intervals (identified as T(2), P(2)) is marked as a "corner" if that change is greater than a predetermined threshold. This is done by measuring the power difference between points T(3), P(3) and T(2), P(2) and between T(2), P(2) and T(1), P(1) to give values A1 and A2 respectively. If the difference B between A1 and A2 exceeds a predetermined value Tol1 then a corner is marked.

Figure 5:
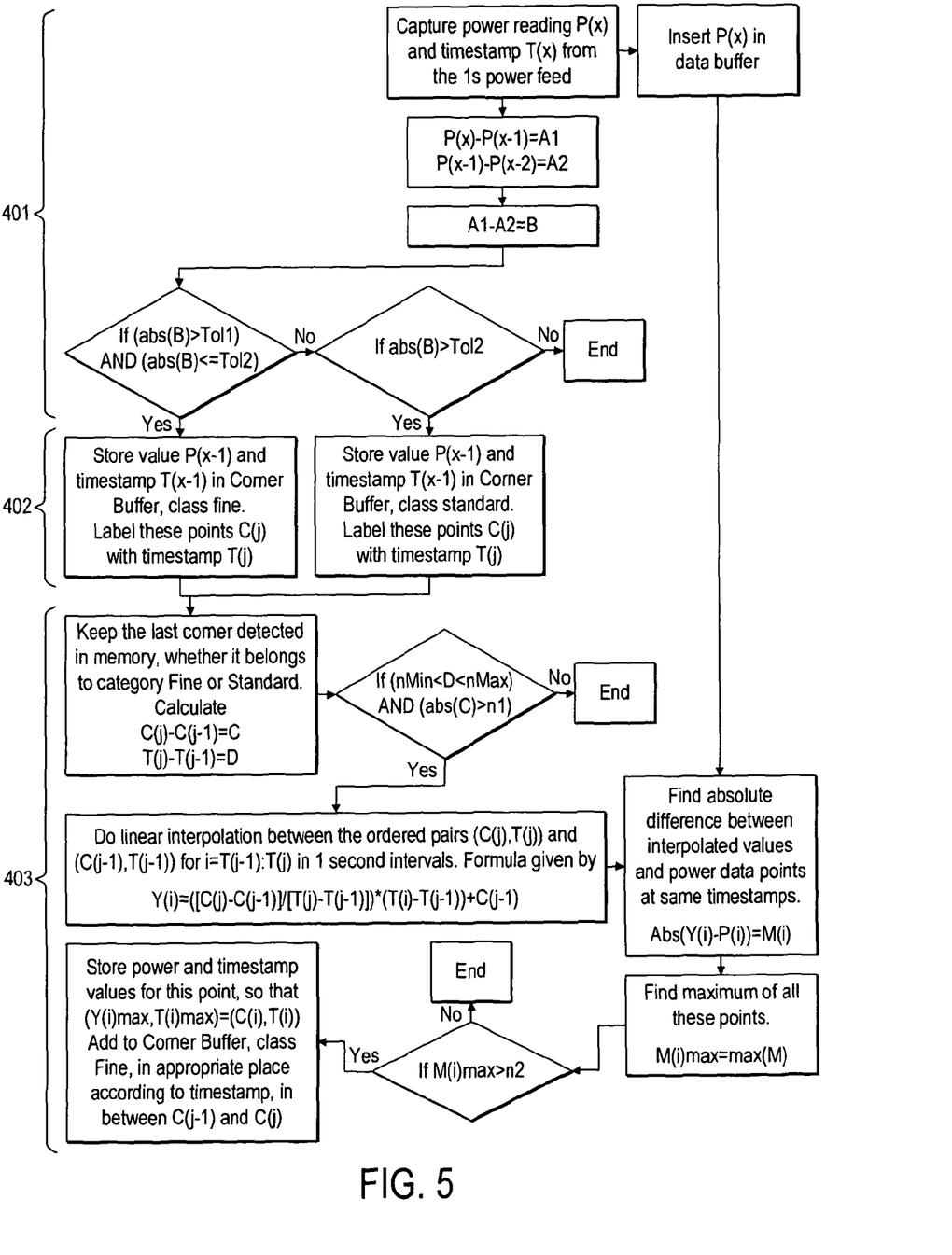
FIG. 5 is a flowchart illustrating the corner detection algorithm.

The operation of the algorithm is illustrated in more detail in FIG. 5 in which:

T(x), T(i) and T(j) represent 32 Bit timestamps

C(x), C(j) and Y(i) represent 16 Bit power readings at a corner

Tol1. Tol2 represent integer numerical values (0-100)

A1, A2, B represent 16 Bit power reading differences n1, nMax, nMin, n2 represent 16 Bit numerical values M(i), M(i) max represent 16 Bit numerical values Section 401 of FIG. 5 illustrates identification of corners as described above with reference to FIG. 3.

Section 402 of FIG. 5 illustrates the classification of corners into "Standard" and "Fine" classes depending, respectively, on whether B is greater than predetermined values Tol1 and Tol2 or greater than Tol1 only.

The skilled person will understand how to select the value of the threshold for marking a point as a corner, and the specific value will vary from case to case.

By measuring and identifying these corners in the fixed interval power measurements, and outputting data regarding these corners, the corresponding parameter values and the associated timestamp values, the series of event measurements 5 at variable intervals is produced.

The series of event measurements 5 at variable intervals allows an electricity consumption history to be generated, either in real time from the event measurements 5 as they are produced, or retrospectively from stored event measurements 5, such as the event measurements 5 stored in the memory 6.

Correction

The series of event measurements 5 at variable intervals generated as described above with respect to FIG. 3 and sections 401 and 402 of FIG. 5 contains the majority of corners, however a correction may be applied to identify one or more corners that may have been missed.

Figure 4:
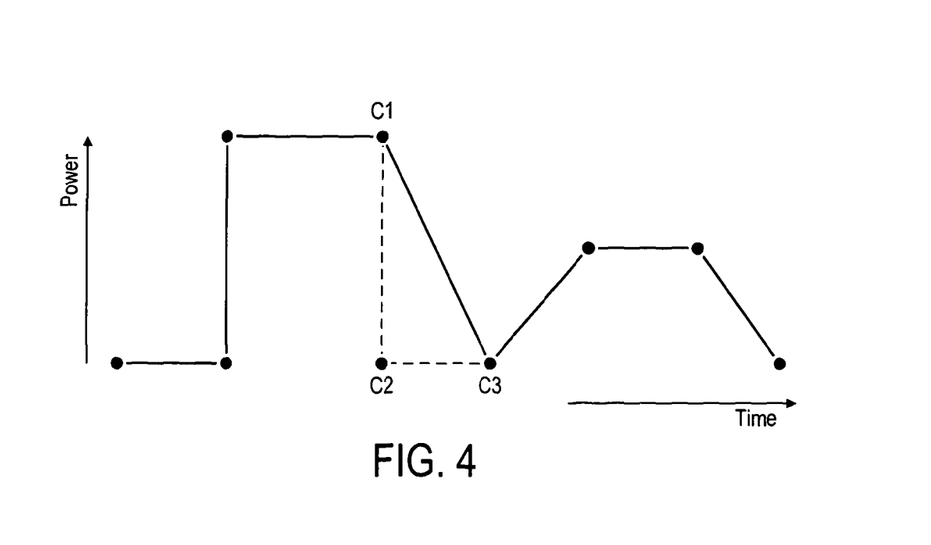
FIG. 4 illustrates schematically the identification of missing corners.

This is illustrated in FIG. 4 which shows a corner C(2) between corners C(1) and C(3) that has been missed by the corner detection algorithm.

A missing corner may be identified if both the power difference (power at C1 minus power at C2) and the time difference (time at C1 minus time at C2) fall outside defined values as illustrated in section 403 of FIG. 5.

In this event, a linear interpolation may be conducted to identify any missing corners, as illustrated in Section 403 of FIG. 5. Referring to FIG. 4, missing corner C3 should be inserted at the point giving the most acute angle between lines C1-C2 and C2-C3.

User Display

Figure 2:
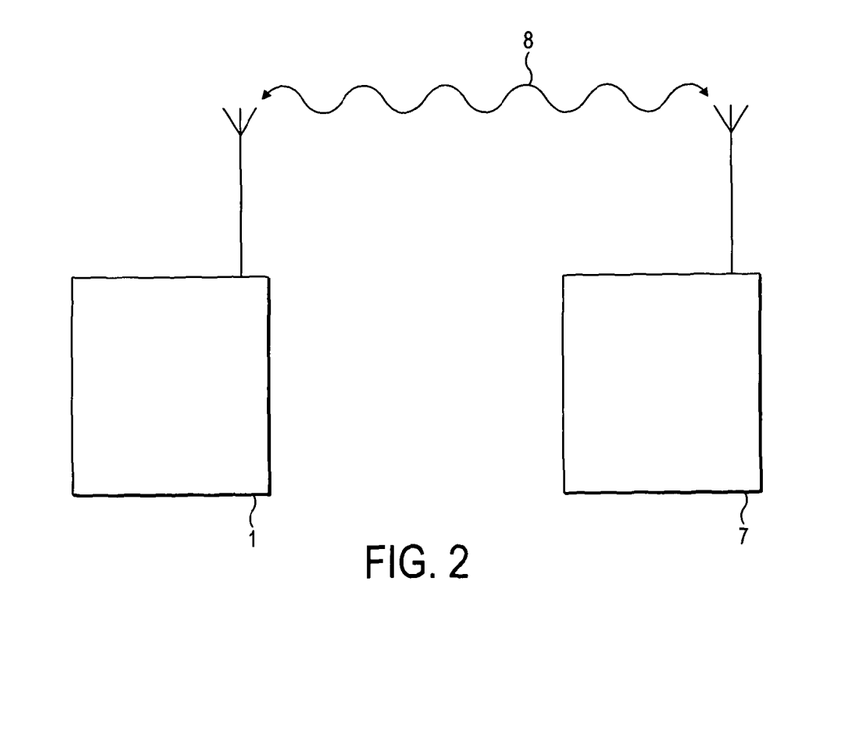
FIG. 2 is a diagram of a smart meter and associated user display unit according to the invention.

As shown in FIG. 2, in a preferred embodiment of the present invention the smart meter 1 is associated with a user display unit 7. The smart meter 1 and the user display unit 7 are arranged for wireless communication with one another through a wireless communication link 8. Suitable wireless communication techniques and wireless communication components to be included in the smart meter 1 and user display unit 7 are well known and need not be discussed in detail here.

The user display unit 7 could be a user display unit as disclosed in WO 2008/142425.

In operation, the smart meter 1 sends the variable interval event measurements to the user display unit 7 through the wireless communication link 8. This can be carried out as a "push" type system where the smart meter 1 sends each new variable interval event measurement to the user display unit 7 each time said new variable interval event measurement is generated and stored in the memory 6, or sends any new variable interval event measurements to the user display unit 7 at predetermined times. Alternatively, this can be carried out as a "pull" type system where the user display unit 7 sends a request for data to the smart meter 1 through the wireless communication link 8, and the smart meter 1 responds by sending any new variable interval event measurements to the user display unit 7. In this case the user display unit can send the requests at predetermined times, or based on activity at the user display unit 7.

The user display unit 7 may be a data processor able to process and display the variable interval event measurement data received from the smart meter 1. The user display unit 7 is able to reconstruct the power consumption measured by the smart meter 1 from the received variable interval event measurements. This reconstructed power consumption can then be displayed to a user. The reconstructed power consumption can also be used for other purposes, as is known in the art, for example tracking total cumulative power consumption over time or identifying the use particular types of appliances being used.

The use of the utilities consumption data compression method according to the present invention provides the advantage that for any selected interval between the fixed interval power measurements the amount of data which must be stored at the smart meter 1, and the amount of data which must be transferred from the smart meter 1 to the user display device 7 can be reduced. Further, the use of the utilities consumption data compression method according to the present invention provides the advantage that the amount of data which must be stored and transferred is not directly related to the frequency of the fixed interval power measurements. Accordingly, the frequency, or interval, of the fixed interval power measurements in any specific application can be selected as required to provide the desired time resolution without having to consider whether the amount of data which will need to be stored or transmitted will be excessive.

The exemplary embodiment described above explains one example of how the present invention may be carried out. It will be understood that further data processing may be carried out in addition to that described. For example, there may be some pre-processing of the power measurements, such as filtering to remove noise, before the event identification is carried out. Further, in addition to the above described lossy compression techniques according to the present invention, the data to be stored or transmitted may also be compressed using a conventional lossless compression technique.

It should be understood that the available bandwidth or data transfer rate from the smart meter 1 to the user display device 7 via the wireless communication link 8 may be relatively low or costly so that the transfer of large amounts of data is highly undesirable.

It will usually be preferred for the user display unit 7 to be in substantially continuous wireless contact with the smart meter 1 so that measurements made by the smart meter 1 are transferred to the user display unit 7 in real time as they are made. However, in some circumstances it may be necessary to transfer historic power consumption data, that is previously recorded power consumption data, from the smart meter 1 to the user display unit 7. This will be necessary if the user display unit 7 has been temporarily out of contact with the smart meter 1, and the power consumption data missed during the lost contact period must be transferred. Further, when a new user display unit 7 is installed to an existing smart meter 1, the user display unit 7 will of course have previously been out of contact with the smart meter 1, and historic power consumption data for a previous period must be transferred. The length of this previous period will vary from case to case.

Further, if a particular previous period of time is of interest to a user it may be necessary to transfer historic power consumption data for this period if it has not been stored in the user display device.

Using a conventional meter in which only a cumulative total of consumed energy is stored, these data transfers could not be made as the required data would not be present on the meter. Further, using a known smart meter where power measurement readings are stored at fixed intervals it can be very difficult to provide the desired information to the user display device because of the every large amount of power readings which must be transferred, and also because it may be difficult or impossible to determine what time any particular power reading corresponds without working back from the most recent data through all of the series of historic data in sequence, which will require a large amount of processing.

These problems can be overcome by the present invention because the utilities consumption data compression method of the present invention dramatically reduces the amount of information that must be transferred, and because each variable interval event measurement is stored in association with a timestamp so that the specific time of the measurement can be easily determined.

In the above described embodiment electrical power consumption is measured. It will be understood that power and energy are closely related so that the skilled person will readily understand how to use the power consumption values to determine values of consumed energy. Further, it will be understood that measured power consumption can be expressed or defined directly in terms of power, or indirectly in terms of the amount of energy consumed since the preceding measurement, provided that the time between the successive measurements is known.

In a preferred embodiment the user display device 7 is able to make the following requests for the smart meter 1 to provide information:

Request all historic measurement data between two specific times;

Request all historic measurement data from the start of reading to a specific time;

Request all historic measurement data from the start of reading to the current time; and Request all historic measurement data from a specific time to the current time.

The precise format of such requests will depend upon the details of any specific implementation. However, the skilled person will readily understand how such simple time based requests can be made and understood.

In order to allow the user display device 7 to predict the amount of data which will be provided in response to each of the above requests the user display device 7 is also able to make the following queries for the smart meter 1 to answer:

Query how much historic data is stored on the meter in total; and

Query how much historic data is stored on the meter between any two times.

It should be noted that in this query "any two times" includes the installation time of the smart meter and the current time, so that this query can be used to predict the amount of data which will be provided in response to each of the above requests by defining appropriate times.

This allows the user display device 7 to judge whether a request for data over a particular time range should be proceeded with, or whether the time range should be reduced. As discussed above, the transfer of a large amount of data may take a long time, so the user display device 7 may prefer to request a small amount of data at a time in order to allow requests for different types of historical data, or other tasks, to be interleaved. For example, a newly installed user display device 7 could gradually obtain historic data in segments working backwards from the present time when it was not busy with other tasks.

Where data is requested starting from a specific time, the smart meter 1 will provide measurement data starting from the closest variable interval event measurement preceding the specific time in order to ensure that no data is missed if the specified time does not coincide with a variable interval event measurement, which will usually be the case.

In order to allow the user display device 7 to control what is recorded as variable interval event measurements by the smart meter 1 to provide the required information the user display device 7, the user display device 7 is also able to query what settings are currently being used by the event identifying device, and to set the settings to be used in future.

This will allow the user display device 7 to determine and set the compression threshold used by the smart meter 1.

Finally, the user display device 7 can instruct the smart meter 1 to stop sending previously requested historic data.

The above description refers to historic data. If the smart meter is able to make predictions of future utilities consumption, the historic data may include data regarding this predicted future consumption.

As an alternative to the above time based requests the user display device 7 may define the requested data in terms of a specific number of variable interval measurements before or after a specific time. In this case the maximum amount of data that will be received in response to the request is known in advance because the specified number is the maximum number of data entries which will be received.

The smart meter 1 is arranged to be able to supply the requested information in response to the respective requests and queries, and to allow remote setting of the event identifying device.

The precise operation of the smart meter in responding to the requests and queries will depend upon the details of any specific implementation. However, the skilled person will readily understand how such simple time based requests can be made and responded to. Further, since each stored variable interval event measurement is stored in association with a timestamp the skilled person will readily understand how time based selection and sorting of the measurements, and assessment of the amount of stored data, can be carried out.

Preferably, when the reply to an information request is a large quantity of data the smart meter sends breaks the reply into a series of separate responses. This may be done by the smart meter comparing the size of the response to a threshold. Alternatively, the user display device 7 can specify the maximum size of each response section, or of the entire response, when sending the request. The separate responses can then be sent separately, or together, as convenient.

If a part of the reply to an information request is not received, it is easy to identify which parts are missing and resend them because each variable interval event measurement has an associated timestamp.

It is preferred that the smart meter and user display device should be able to support all of the requests and queries set out above. However, in some applications it may be sufficient for only some of these requests and queries to be available.

The above description describes the processing, compression, storage and delivery of a single data stream of electrical power consumption data. This is only by way of example, the present invention is also applicable to other parameters. Further, the smart meter may generate, process, compress, store and deliver multiple data streams relating to respective different parameters, and each data stream can be independently processed, stored and queried. The different parameters may be measured at the same or different fixed measurement intervals, as appropriate to the different parameters.

The different data streams relating to the different parameters may be separately processed to identify events and stored separately. Alternatively, the fixed interval measurements in the different data streams relating to the different parameters may be processed together to identify events and/or stored together. For example, a smart meter measuring real power, reactive power, voltage, current and frequency of an electrical utility supply at respective fixed intervals could process the real power and reactive power to identify events, and when an event is identified store the real power and reactive power values, and the voltage, current and frequency values, together with the timestamp.

Typically, the user display device is a domestic client display able to provide real time and historical displays and analyses of utility consumption to a domestic user.

The user display device may be portable. In this case the user display device may often be out of contact with the smart meter.

In the above described embodiment of the invention the user display device is connected to the smart meter by a wireless communication link. As an alternative it would be possible for the user display device to be connected to the smart meter by a direct wired connection. The user display device could even be combined with the smart meter in a single unit.

The above described embodiment describes the invention as employed by a smart meter in communication with a user display device. The smart meter could additionally, or alternatively, be connected to other client devices such as a user PC, a utility supplier billing computer, or third party data collection centre, either directly. Similarly, the user display device could be connected to client devices such as a user PC, a utility supplier billing computer, or third party data collection centre. These connections can conveniently be made through a user internet connection. The smart meter will usually have an advanced metering infrastructure (AMI) or automatic metering system (AMR) data connection, but it will usually be too costly to use these to transfer data to client devices.

In the above described embodiment of the invention a single user display device is connected to a single smart meter by a wireless communication link. As an alternative it would be possible for a single user display device to be connected to multiple smart meters. The multiple smart meters could measure different utilities, and/or supply of the same utility to different households, or other settings that receives their own discrete utilities, of interest to the user. As another alternative it would be possible for multiple user display devices, or other client devices, to be connected to a single smart meter. In this case, data requested by the different devices can be delivered as a series of responses.

The invention has been discussed primarily with respect to consumption of electricity, however it will be appreciated that the methods described herein can equally be applied to consumption of water or gas supplied to a household.

Consumption of water and gas can be measured using techniques that are well known to the skilled person, for example based on use of water and gas meters. Water and gas consumption, in particular water consumption, may be measured at a lower rate, for example at least once every 300 seconds or at least once every 60 seconds, in order to generate water consumption data that may be used to identify events associated with consumption of water. The rate of flow of water or gas at each time interval may be measured, along with the total volume consumed over time in a manner analogous to power and energy measurements of electricity consumption. Additionally or alternatively, water and gas consumption may be measured at measurement points after intervals of volume consumption rather than intervals of time, for example a measurement of time elapsed for each unit volume (e.g. liter) of water to be consumed.

The apparatus described above may be implemented at least in part in software. Those skilled in the art will appreciate that the apparatus described above may be implemented using general purpose computer equipment or using bespoke equipment.

The hardware elements, operating systems and programming languages of such computers are conventional in nature, and it is presumed that those skilled in the art are adequately familiar therewith. Of course, the server functions may be implemented in a distributed fashion on a number of similar platforms, to distribute the processing load.

Here, aspects of the methods and apparatuses described herein can be executed on a mobile station and on a computing device such as a server. Program aspects of the technology can be thought of as "products" or "articles of manufacture" typically in the form of executable code and/or associated data that is carried on or embodied in a type of machine readable medium. "Storage" type media include any or all of the memory of the mobile stations, computers, processors or the like, or associated modules thereof, such as various semiconductor memories, tape drives, disk drives, and the like, which may provide storage at any time for the software programming. All or portions of the software may at times be communicated through the Internet or various other telecommunications networks. Such communications, for example, may enable loading of the software from one computer or processor into another computer or processor. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to tangible non-transitory "storage" media, terms such as computer or machine "readable medium" refer to any medium that participates in providing instructions to a processor for execution.

Hence, a machine readable medium may take many forms, including but not limited to, a tangible storage carrier, a carrier wave medium or physical transaction medium. Non-volatile storage media include, for example, optical or magnetic disks, such as any of the storage devices in computer(s) or the like, such as may be used to implement the encoder, the decoder, etc. shown in the drawings. Volatile storage media include dynamic memory, such as the main memory of a computer platform. Tangible transmission media include coaxial cables; copper wire and fiber optics, including the wires that comprise the bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will appreciate that while the foregoing has described what are considered to be the best mode and, where appropriate, other modes of performing the invention, the invention should not be limited to specific apparatus configurations or method steps disclosed in this description of the preferred embodiment. It is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings. Those skilled in the art will recognize that the invention has a broad range of applications, and that the embodiments may take a wide range of modifications without departing from the inventive concept as defined in the appended claims.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:

1. A method of storing data regarding parameter values comprising the steps of:
    making a series of measurements of parameter values at times separated by predetermined time intervals;
    processing, via a processor, the series of measurements of parameter values made at predetermined time intervals to identify events at different times, the processing comprising determining a gradient of change of parameter value between each consecutive measurement of parameter value, and identifying as events times where a change in successive gradients exceeds a threshold value;
    generating a further series of measurements of parameter values at each of said different times; and
    storing in memory each of said further series of measurements of parameter values in association with said respective different time.

2. The method according to claim 1, wherein said predetermined time intervals are fixed time intervals.

3. The method according to claim 1, wherein each of said further series of measurements of parameter values is stored together with measurements of values of additional parameters measured at said respective different time.

4. The method according to claim 1, wherein said further series of measurements of parameter values are derived from said series of measurements of parameter values.

5. The method according to claim 4, wherein said further series of measurements of parameter values are derived from said series of measurements of parameter values using a selection process.

6. The method according to claim 1, wherein the intervals between measurements is in the range 0.01 to 60 seconds.

7. The method according to claim 1, wherein said parameter values are utilities consumption values.

8. The method according to claim 7, wherein the utility is selected from gas, electricity and water.

9. The method according to claim 8, wherein the utility is electricity and the electricity consumption values include measured values of real power, reactive power, or both reactive power and real power.

10. The method according to claim 1, further comprising transmitting the stored measurements of parameter values and associated times to a data processor.

11. The method according to claim 10, wherein the stored measurements of parameter values and associated times are transmitted by wired or wireless transmission.

12. The method according to claim 10, wherein the data processor is a user display device.

13. The method according to claim 12, wherein the user display device is a domestic user display device.

14. An apparatus adapted to store data regarding electricity consumption comprising:
    means for making a series of measurements of electricity consumption values at times separated by predetermined time intervals;
    for processing the series of measurements of electricity consumption values made at predetermined time intervals to identify events at different times, the processing comprising determining a gradient of change of parameter value between each consecutive measurement of parameter value, and identifying as events times where a change in successive gradients exceeds a threshold value;
    for generating a further series of measurements of electricity consumption values at each of said different times;
    means for storing each of said further series of measurements of electricity consumption values in association with said respective different time; and
    means for transmitting the stored measurements of parameter values and associated times to a data processor.

15. A system comprising:
    an apparatus adapted to store data regarding electricity consumption comprising:
        means for making a series of measurements of electricity consumption values at times separated by predetermined time intervals;
        means for processing the series of measurements of electricity consumption values made at predetermined time intervals to identify events at different times, the processing comprising determining a gradient of change of parameter value between each consecutive measurement of parameter value, and identifying as events times where a change in successive gradients exceeds a threshold value;
        means for generating a further series of measurements of electricity consumption values at each of said different times;
        means for storing each of said further series of measurements of electricity consumption values in association with said respective different time; and
        means for transmitting the stored measurements of parameter values and associated times to a data processor; and
    a data processor adapted to receive the transmitted stored measurements of parameter values and associated times.

16. The system according to claim 15, wherein the data processor is a user display device.

17. The system according to claim 16, wherein the user display device is a domestic user display device.

18. An article of manufacture comprising:
    a non-transitory machine-readable storage medium; and
    executable program instructions embodied in the machine readable storage medium that when executed by a programmable system causes the system to perform the function of storing data regarding utilities consumption comprising the steps of:

making a series of measurements of parameter values at times separated by predetermined time intervals;

processing the series of measurements of parameter values made at predetermined time intervals to identify events at different times, the processing comprising determining a gradient of change of parameter value between each consecutive measurement of parameter value, and identifying as events times where a change in successive gradients exceeds a threshold value;

generating a further series of measurements of parameter values at each of said different times; and storing each of said further series of measurements of parameter values in association with said respective different time.

* * * * *